United States Patent
Jo et al.

(10) Patent No.: US 6,802,872 B2
(45) Date of Patent: Oct. 12, 2004

(54) HAIRDYE COMPOSITION CONTAINING METALLIC COMPOUND

(75) Inventors: Bong Lim Jo, Asan-Si (KR); Hyun Jin Jo, Asan-Si (KR); Hey Young Choi, Asan-Si (KR)

(73) Assignee: Dong Sung Pharmaceuticals, Co., Ltd., Seoul (KR)

( * ) Notice: Subject to any disclaimer, the term of this patent is extended or adjusted under 35 U.S.C. 154(b) by 39 days.

(21) Appl. No.: 10/097,502

(22) Filed: Mar. 15, 2002

(65) Prior Publication Data

US 2002/0133887 A1 Sep. 26, 2002

(30) Foreign Application Priority Data

Mar. 21, 2001 (KR) .................................. 2001-0014756

(51) Int. Cl.[7] ................................................. A61K 7/13
(52) U.S. Cl. ..................... 8/405; 8/407; 8/452; 8/602; 8/611; 8/624; 8/685
(58) Field of Search ........................... 8/405, 407, 452, 8/602, 611, 624, 685

(56) References Cited

U.S. PATENT DOCUMENTS 6,099,592 A * 8/2000 Vidal et al. ..................... 8/409
6,143,286 A * 11/2000 Bhambhani et al. ........ 424/70.1

* cited by examiner

Primary Examiner—Brian P Mruk
Assistant Examiner—Eisa Elhilo
(74) Attorney, Agent, or Firm—McGuireWoods LLP

(57) ABSTRACT

A hairdye composition containing a metallic compound such as $AgNO_3$ and $C_3H_5AgO_3$ is disclosed, in which the metallic compound is mixed with a cream type composition that can be applied to hair, thereby gradually coloring gray hair. To this end, $AgNO_3$ is composed of 0.05~10.0 wt % based on total weight and $C_3H_5AgO_3$ is composed of 0.05~10.0 wt % based on total weight.

4 Claims, 4 Drawing Sheets

After 1 day        2 days        3 days        5 days (condition: leave eight hours a day as it is after applied)

sectional structure of hair on the first day after applied sectional structure of hair on the second day after applied sectional structure of hair on the third day after applied sectional structure of hair on the fifth day after applied

HAIRDYE COMPOSITION CONTAINING METALLIC COMPOUND

BACKGROUND OF THE INVENTION

The file of this patent contains at least one drawing executed in color. Copies of this patent with the color drawings will be provided by the U.S. Patent and Trademark Office upon request and payment of the necessary fee.

1. Field of the Invention

The present invention relates to a hairdye composition containing a metallic dye, which colors a gray hair or decolored hair in a natural hair color, and more particularly to a hairdye composition including a metallic compound in which $AgNO_3$ and $C_3H_5AgO_3$ are used as main components of the metallic compound.

2. Discussion of the Related Art

Generally, a hairdye is used to recover aged gray hair to an original hair color. Otherwise, the hairdye is used to change the original hair color to a desired color and vice versa.

The hairdye is divided into three types in accordance with its conditions fixed to hair; a temporary hairdye, a semi-permanent hairdye, and a permanent hairdye.

The permanent hairdye is constructed in such a manner that a coloring agent is permeated into epidermis of hair to precipitate coloring molecules into hair cortex. Also, the permanent hairdye enables decoloring and coloring of hair by means of permeation and oxidation. Examples of the permanent hairdye include a vegetable dye, a metallic dye, a mixture dye, and an oxidation dye(synthetic dye). Of them, the oxidation dye is mostly used as the permanent hairdye. However, since the oxidation dye is likely to stimulate the skin, it is difficult for people having a sensitive skin to use it. For this reason, the metallic dye which is relatively less susceptible to the skin is on an increasing trend.

An example of the metallic dye used since ancient times is based on lead. This metallic dye based on lead has been used in such a manner that hair is colored in a dark color using a comb made of lead deposited in vinegar. In addition to lead, various metallic compounds have been used to color hair. Mostly used metallic compounds are lead, silver, and copper.

The metallic compounds used to color hair get mixed with sulfur, nickel, or iron to enhance color fixation power. Bismuth, manganese, and cobalt are also used to get mixed with the metallic dyes.

Ammonium thioglycolate, potassium hydrosulfide, ammonium hydrosulfide, sodium hydrosulfide, and pyrogallol are used as couplers when the metallic dye is applied to hair. To enhance coloring effect, there are provided two-type hairdyes divided depending on properties of couplers and contained in two separate vessels. In this case, inconvenience arises in that the hairdyes should separately be applied to hair.

Recently, there is provided one type hairdye made by mixing lead nitrate, ammonia, and sulfur with one another. This hairdye has several problems in that its color fixation power is weak and it may be concerned about lead poisoning in case of long time use in hair.

Furthermore, alkalizer such as ammonia and ammonium thioglycolate, which is used as the metallic dye, swells hair with a strong alkali and makes hair soft so that it is easy to permeate into hair. However, it has a problem in that it should be applied to hair all day and used repeatedly, thereby causing serious damage to hair.

SUMMARY OF THE INVENTION

Accordingly, the present invention is directed to a hairdye composition containing a metallic compound that substantially obviates one or more of the problems due to limitations and disadvantages of the related art.

An object of the present invention is to provide a hairdye composition containing a metallic compound in which $AgNO_3$ and $C_3H_5AgO_3$ are used as main components of the metallic compound, which are used to manufacture silver bromide and disinfectant, to color ceramic ware, and to produce a silver mirror by reduction reaction of an organism.

Another object of the present invention is to provide a hairdye composition containing a metallic compound in which a surfactant such as polyglucoside is added to $AgNO_3$ and $C_3H_5AgO_3$ without a conventional coupler that causes damage to hair, thereby enhancing color fixation power.

Another object of the present invention is to provide a hairdye composition containing a metallic compound of which pH density is adjusted to pH of hair, thereby avoiding damage to hair.

Another object of the present invention is to provide a hairdye composition containing a metallic compound in which one type hairdye simply is applied to hair, thereby coloring hair in a desired color.

Another object of the present invention is to provide a hairdye composition containing a metallic compound in which one type hairdye simply is applied to hair, thereby coloring a desired color in hair.

Another object of the present invention is to provide a hairdye composition that can act as a hair refiner such as hair oil and at the same time can color hair.

Another object of the present invention is to provide a hairdye composition that can avoid heavy metal poisoning such as lead poisoning.

Another object of the present invention is to provide one type hairdye composition that can gradually color hair by repeatedly applying a hairdye to hair every day.

Additional features and advantages of the invention will be set forth in the description which follows, and in part will be apparent from the description, or may be learned by practice of the invention. The objectives and other advantages of the invention will be realized and attained by the scheme particularly pointed out in the written description and claims hereof as well as the appended drawings.

To achieve these and other advantages and in accordance with the purpose of the present invention, as embodied and broadly described, a hairdye composition containing a metallic compound, which includes a metallic dye, a surfactant, alcohol, and a moisturizing agent, is characterized in that the metallic dye is composed of 0.05~10.0 wt % based on total weight and is selected from at least one of $AgNO_3$ and $C_3H_5AgO_3$.

The surfactant is composed of at least one group selected from glyceryl stearate/ceteareth-20/ceteareth-12/cetearyl alcohol/cetyl palmitate, ceteareth-20, ceteareth-12, lauryl glucoside, nonoxynol-10, and cocamide dea.

The alcohol is composed of at least one group selected from cetyl alcohol, stearyl alcohol, oleyl alcohol, and hexyldecanol.

The moisturizing agent is composed of at least one group selected from coco-caprylate/caprate, propylene glycol, and henna.

It is to be understood that both the foregoing general description and the following detailed description are exemplary and explanatory and are intended to provide further explanation of the invention as claimed.

BRIEF DESCRIPTION OF THE ATTACHED DRAWINGS

The invention will be described in detail with reference to the following drawings in which like reference numerals refer to like elements wherein.

DETAILED DESCRIPTION OF THE PREFERRED EMBODIMENTS

Reference will now be made in detail to the preferred embodiments of the present invention, examples of which are illustrated in the accompanying drawings.

EXAMPLE 1

In this embodiment of the present invention, a cream type hairdye composition containing a metallic compound will be described.

Figure 1:
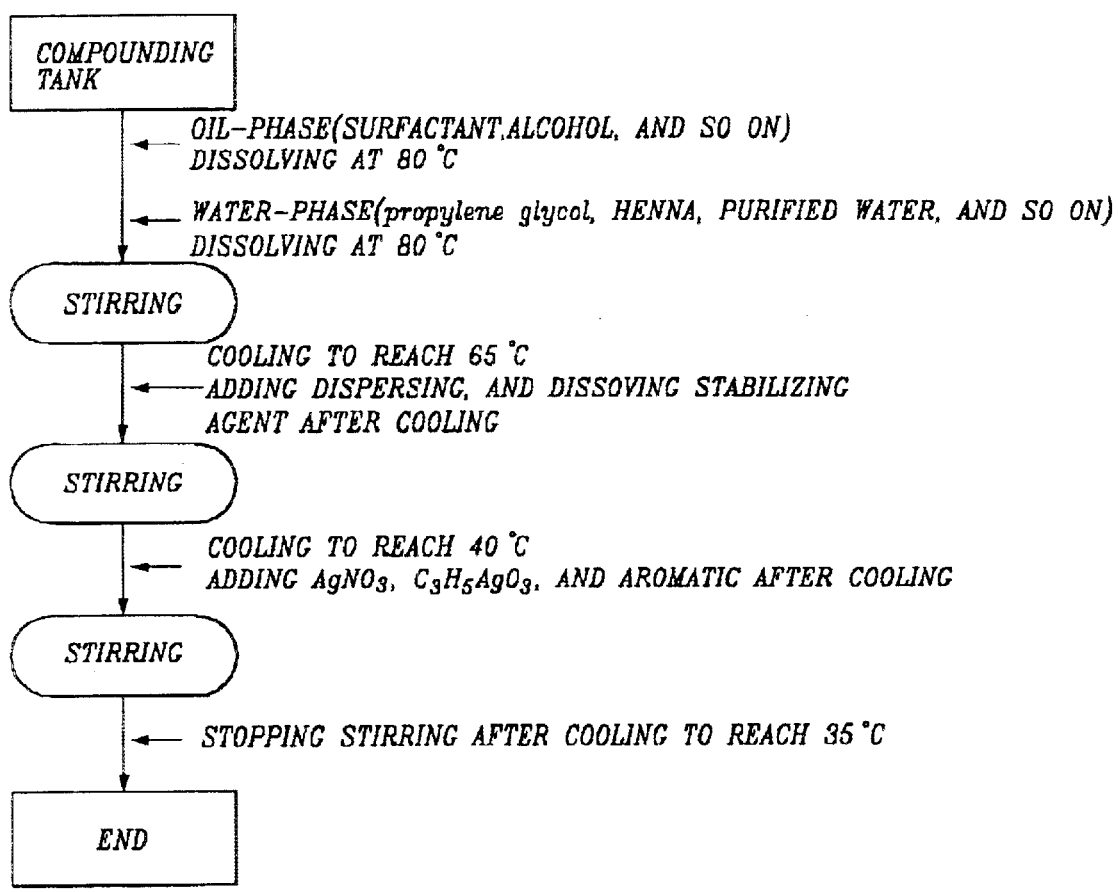
FIG. 1 is a block diagram illustrating processing steps according to the first embodiment of the present invention.

The cream type hairdye composition, as shown in FIG. 1, is composed in such a manner that a surfactant of 2.0~27.0 wt %, alcohol of 1.0~25.0 wt %, and a moisturizing agent of 10.0~26.0 wt % are dissolved between 75° C. and 85° C. within a compounding tank. Subsequently, the dissolved product is mixed with purified water of titer, $AgNO_3$ of 0.05~10.0 wt %, and $AgNO_3$ and $C_3H_5AgO_3$ of 0.05~10.0 wt %. The resultant product is then dissolved again.

In more detail, the surfactant is composed of glyceryl stearate/ceteareth-20/ceteareth-12/cetearyl alcohol/cetyl palmitate of 6.0 wt %, ceteareth-20 of 5.0 wt %, ceteareth-20 of 1.0 wt %, and lauryl glucoside of 1.0 wt %. the alcohol is composed of cetyl alcohol of 3.0 wt %, stearyl alcohol of 3.0 wt %, and oleyl alcohol of 6.0 wt %. The moisturizing agent is composed of coco-caprylate/caprate of 5.0 wt %, propylene glycol of 1.0 wt %, and henna of 20.0 wt %.

The dissolved product is sufficiently stirred so that it is cooled to reach about 65° C. A stabilizing agent such as dimethicone of 0.3 wt % and cyclomethicone of 2.0 wt % is added to the resultant product, thereby dispersing and dissolving the product.

Subsequently, once the product is cooled to reach 40° C., $AgNO_3$ and $C_3H_5AgO_3$ are added to the product by 3.5 wt %, respectively. Other additives such as hydrogen peroxide of 0.04 wt %, phenacetin of 0.05 wt %, methylparaben of 0.15 wt %, bht of 0.05%, propylparaben of 0.10 wt %, ethylhexyl methoxycinnamate of 2.0 wt %, and mineral oil of 3.0 wt % are added to the product and then stirred. The resultant product is cooled again to reach 30° C.

In this embodiment of the present invention, $AgNO_3$ and $C_3H_5AgO_3$ have been added to the product by 3.5 wt %, respectively. However, either of $AgNO_3$ and $C_3H_5AgO_3$ may be added to the product, thereby fabricating the cream type hairdye composition that can achieve the object of the present invention.

EXAMPLE 2

In this embodiment of the present invention, a liquid type hairdye composition containing a metallic compound will be described.

Figure 2:
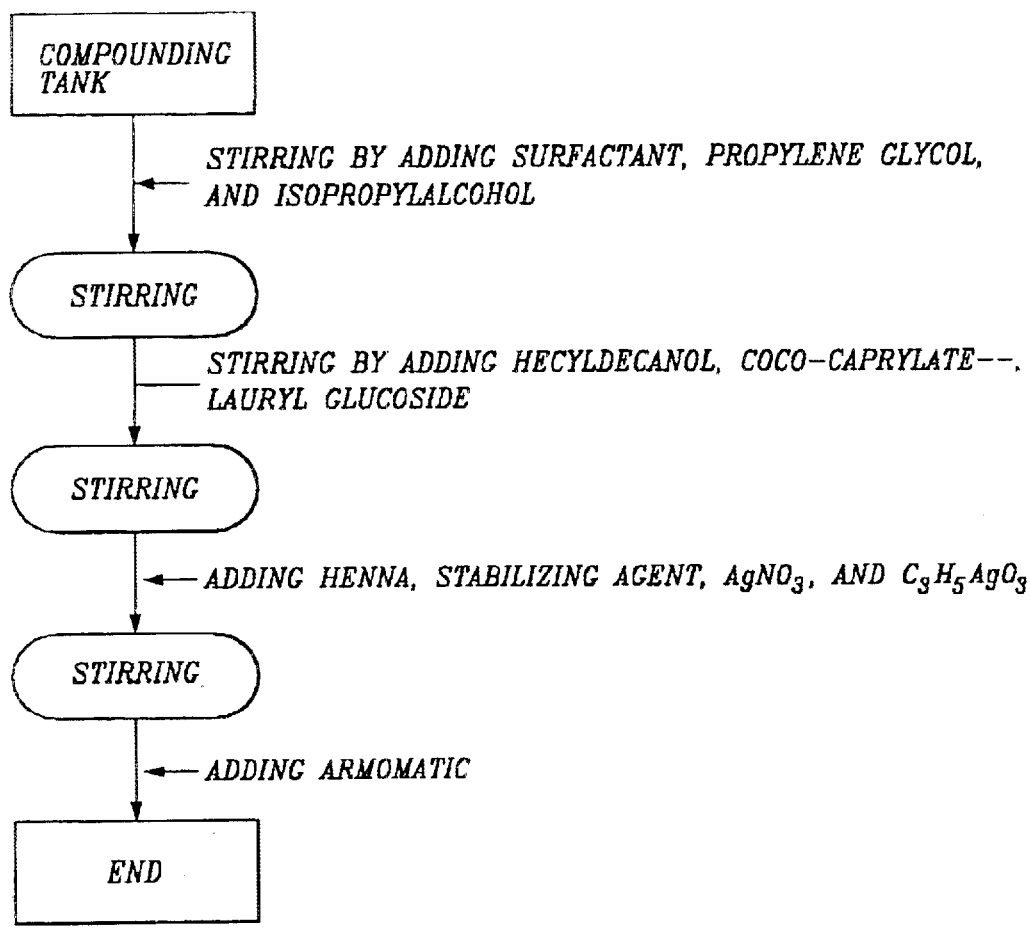
FIG. 2 is a block diagram illustrating processing steps according to the second embodiment of the present invention.

The liquid type hairdye composition, as shown in FIG. 2, is composed in such a manner that a surfactant, propylene glycol, and isopropylalcohol are added to a compounding tank and then stirred. Subsequently, hecyldecanol, cococaprylate/caprate, and lauryl glucoside are added thereto and then stirred.

Afterwards, henna, a stabilizing agent, $AgNO_3$, and $C_3H_5AgO_3$ are added to the resultant product and then stirred. An aromatic is finally added thereto.

In more detail, the surfactant is composed of nonoxynol-10 of 22.0 wt % and cocamide dea of 5.0 wt %. the alcohol is composed of hexyldecanol of 6.0 wt % and isopropylalcohol of 10.0 wt %. the moisturizing agent is composed of cococaprylate/caprate of 5.0 wt %, propylene glycol of 3.0 wt %, and henna of 18.0 wt %.

Also, $AgNO_3$ and $C_3H_5AgO_3$ are added to the product by 6.5 wt %, respectively. Other additives include hydrogen peroxide of 0.04 wt %, phenacetin of 0.05 wt %, lauryl glucoside of 1.0 wt %, an aromatic of titer, and purified water.

In this embodiment of the present invention, $AgNO_3$ and $C_3H_5AgO_3$ have been added to the product by 6.5 wt %, respectively. However, either of $AgNO_3$ and $C_3H_5AgO_3$ may be added to the product.

Furthermore, pH of the hairdye composition according to the present invention is adjusted similarly to that of hair so that no damage to hair occurs.

After the one type hairdye composition containing a metallic compound, such as cream type and liquid type, was fabricated, it was subject to hair test repeatedly once every day for five days. As a result, it was noted that hair color was changed as shown in FIG. 3.

Figure 3:
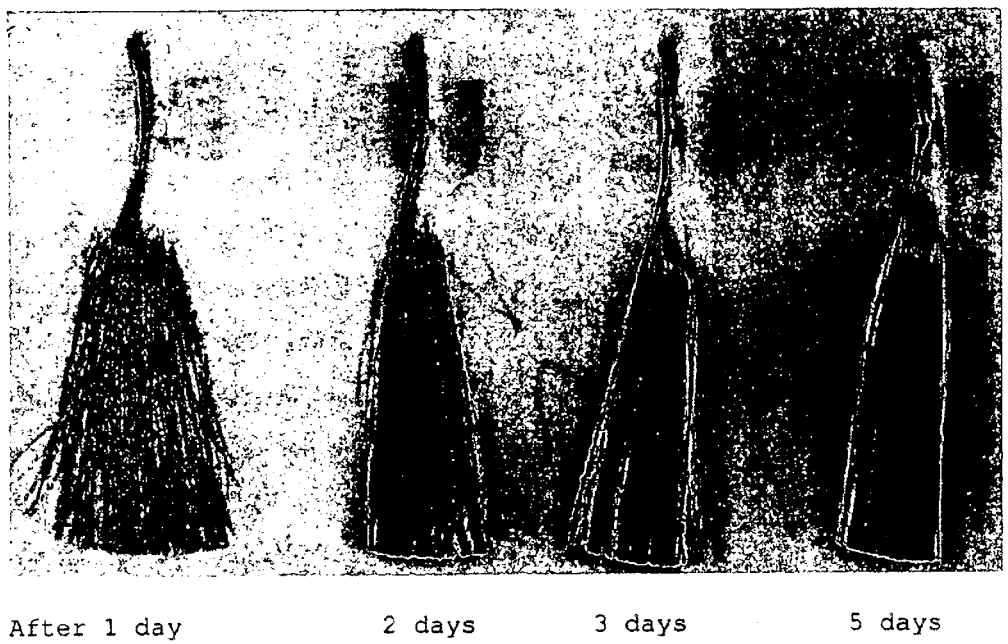
FIG. 3 illustrate dyeing state of hair in temporal order using a hairdye composition according to the present invention.
Figure 4A:
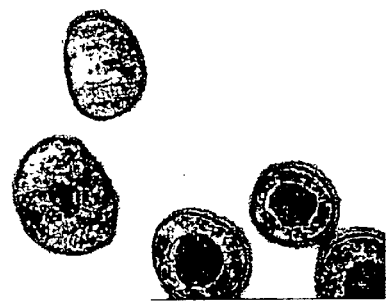
FIGS. 4a to 4d illustrate sectional structures of hair of FIG. 3.
Figure 4B:
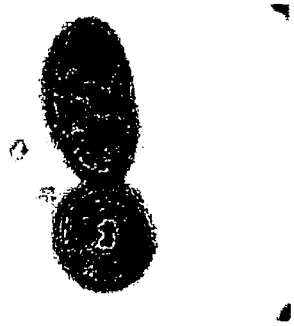
Figure 4C:
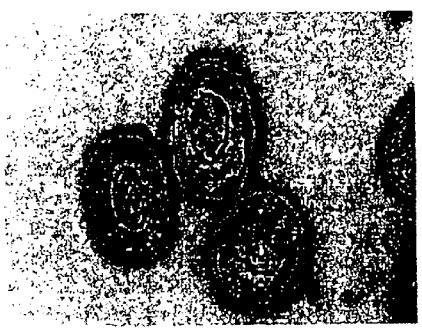
Figure 4D:
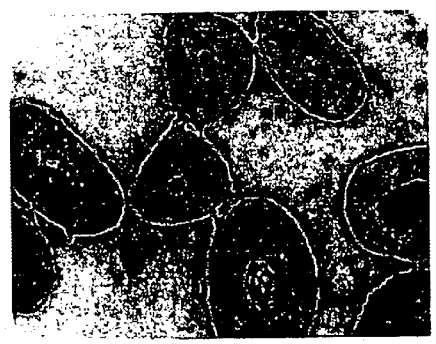

As will be apparent from FIGS. 4a to 4d showing a sectional structure of hair of FIG. 3, the hairdye composition was permeated into hair as time passes.

As aforementioned, the hairdye composition containing a metallic compound according to the present invention has the following advantages.

The hairdye composition containing a metallic compound according to the present invention is manufactured by adding a surfactant such as polyglucoside to $AgNO_3$ and $C_3H_5AgO_3$ without using a separate coupler, $AgNO_3$ and $C_3H_5AgO_3$ being used to manufacture silver bromide and disinfectant, to color ceramic ware, and to produce a silver mirror by reduction reaction of an organism. Thus, heavy metal poisoning can be avoided in the process of coloring hair, and damage to hair can be prevented from occurring, thereby enhancing color fixation power. At the same time, it is possible to dye hair in a desired color by simply applying one type hairdye to hair.

The foregoing embodiments are merely exemplary and are not to be construed as limiting the present invention. The present teachings can be readily applied to other types of apparatuses. The description of the present invention is intended to be illustrative, and not to limit the scope of the claims. Many alternatives, modifications, and variations will be apparent to those skilled in the art.

What is claimed is:

1. A hair dye composition, comprising:
   a metallic compound which includes a metallic dye, a surfactant, alcohol, and a moisturizing agent, wherein the metallic dye ranges from 0.05 to about 10.0 wt % based on total weight and the metallic dye comprises at least one of $AgNO_3$ and $C_3H_5AgO_3$.

2. The hair dye composition as claimed in claim 1, wherein the surfactant is selected from the group consisting of glyceryl stearate/ceteareth-20/ceteareth-12/cetearyl alcohol/cetyl palmitate, ceteareth-20, ceteareth-12, lauryl glucoside, nonoxynol-10, and cocamide dea.

3. The hair dye composition as claimed in claim 1, wherein the alcohol is selected from the group consisting of cetyl alcohol, stearyl alcohol, oleyl alcohol, and hexyldecanol.

4. The hair dye composition as claimed in claim 1, wherein the moisturizing agent is selected from the group consisting of coco-caprylate/caprate, propylene glycol, and henna.

* * * * *